US009467770B2

(12) United States Patent
Grone et al.

(10) Patent No.: US 9,467,770 B2

(45) Date of Patent: Oct. 11, 2016

(54) HANDSET OR HEADSET

(71) Applicant: Sennheiser electronic GmbH & Co. KG, Wedemark (DE)

(72) Inventors: Christian Grone, Wedemark (DE); Stefan Marten, Wedemark (DE); Oliver Pabst, Hamburg (DE)

(73) Assignee: Sennheiser electronic GmbH & Co. KG, Wedemark (DE)

( * ) Notice: Subject to any disclaimer, the term of this patent is extended or adjusted under 35 U.S.C. 154(b) by 0 days.

(21) Appl. No.: 14/451,547

(22) Filed: Aug. 5, 2014

(65) Prior Publication Data

US 2015/0078570 A1 Mar. 19, 2015

(30) Foreign Application Priority Data

Aug. 14, 2013 (DE) ........................ 10 2013 216 133

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04R 27/04*** | (2006.01) |
| ***H04B 15/00*** | (2006.01) |
| ***H04R 3/00*** | (2006.01) |
| ***H04R 1/10*** | (2006.01) |
| ***G10K 11/178*** | (2006.01) |

(52) U.S. Cl.

CPC ......... *H04R 1/1083* (2013.01); *G10K 11/1788* (2013.01); *H04R 1/10* (2013.01); *G10K 2210/1081* (2013.01); *G10K 2210/3035* (2013.01); *G10K 2210/3219* (2013.01); *H04R 2201/107* (2013.01); *H04R 2410/05* (2013.01); *H04R 2460/01* (2013.01)

(58) Field of Classification Search

CPC ................. G10K 11/1788; G10K 2210/1081; G10K 2210/3035; G10K 2210/3219; H04R 1/04; H04R 1/1083; H04R 2460/01; H04R 3/00

USPC ........................................................ 381/71.6

See application file for complete search history.

(56) References Cited

U.S. PATENT DOCUMENTS 4,987,598 A * 1/1991 Eriksson ............ G10K 11/1784 381/71.11

5,706,360 A * 1/1998 Khandekar .......... H04R 1/1008 351/123

5,815,582 A * 9/1998 Claybaugh ......... G10K 11/1784 381/71.6

(Continued)

FOREIGN PATENT DOCUMENTS

| | | |
|---|---|---|
| DE | 102007013719 | 9/2008 |
| JP | 2002-101483 | 4/2002 |
| JP | 2012-244617 | 10/2012 |

*Primary Examiner* — Khai N Nguyen

(74) *Attorney, Agent, or Firm* — Frommer Lawrence & Haug LLP

(57) ABSTRACT

There is provided a headphone or headset comprising at least one housing, at least one microphone for detecting interference sound, at least one active noise compensation unit for implementing active noise compensation based on the interference sound detected by the at least one microphone and for the output of a compensation signal. The headphone or the headset has at least one electroacoustic reproduction transducer for output of the compensation signal from the noise compensation unit and a circumaural cushion having a recess for receiving a spectacles side arm. The active noise compensation unit is adapted in noise compensation to take account of the effect of the recess in the ear cushion.

9 Claims, 1 Drawing Sheet

(56) References Cited

U.S. PATENT DOCUMENTS

| | | | | |
|---|---|---|---|---|
| 6,532,296 | B1 * | 3/2003 | Vaudrey | G10K 11/1788 381/371 |
| 7,317,802 | B2 | 1/2008 | Wurtz | |
| 2010/0119076 | A1 * | 5/2010 | Monk | A61F 11/14 381/71.6 |
| 2010/0166203 | A1 * | 7/2010 | Peissig | G10K 11/1788 381/71.6 |
| 2012/0278070 | A1 * | 11/2012 | Herve | G10L 21/0208 704/226 |
| 2013/0129106 | A1 * | 5/2013 | Sapiejewski | H04R 1/105 381/71.6 |
| 2013/0208908 | A1 * | 8/2013 | Theiler | G10K 11/178 381/71.6 |
| 2014/0126734 | A1 * | 5/2014 | Gauger, Jr. | H04R 3/002 381/71.6 |

* cited by examiner

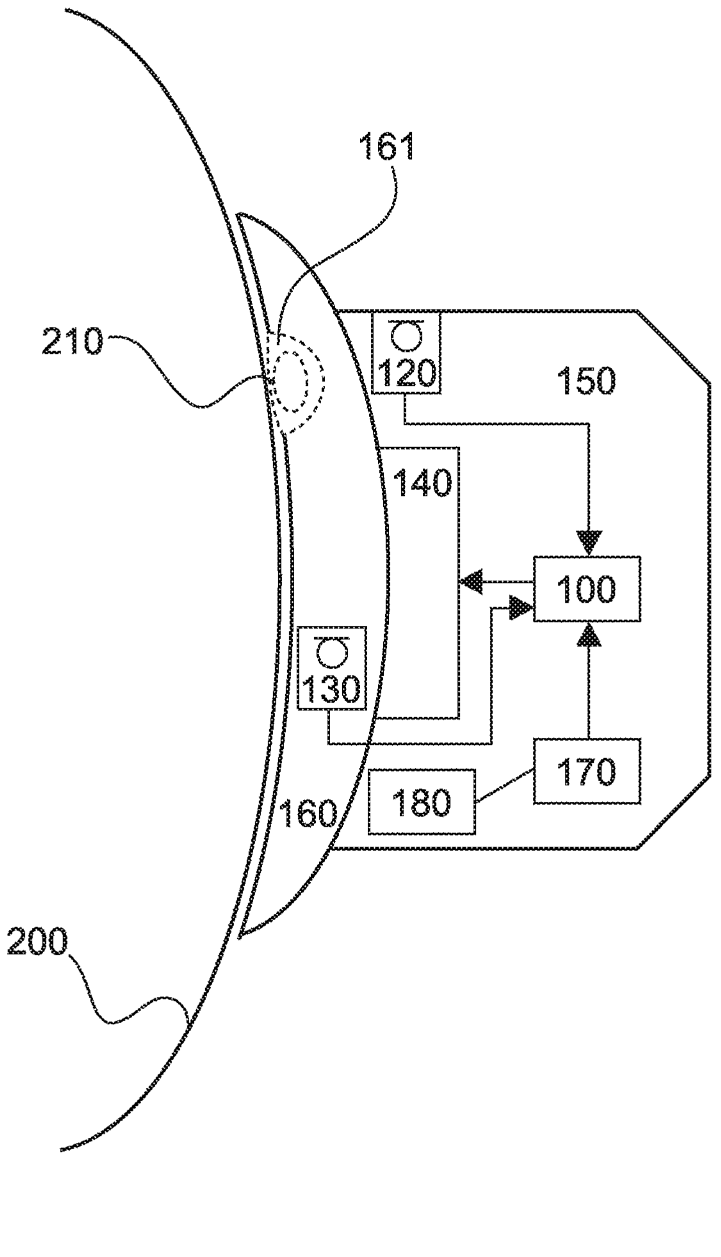
161
210
120
150
140
100
130
170
180
160
200

HANDSET OR HEADSET

The present application claims priority to German Patent Application No. DE 102013216133.6 filed on Aug. 14, 2013, the disclosure of which is incorporated herein by reference in its entirety.

FIELD OF THE INVENTION

The present invention concerns a headphone or a headset.

It is noted that citation or identification of any document in this application is not an admission that such document is available as prior art to the present invention.

The use in particular of headphones or headsets with circumaural ear cushions is sufficiently known. Particularly in a noise-filled environment it is desirable to implement active noise compensation in the headphone or the headset. For good active noise compensation it is important for the ear cushion to fit snugly to the head of a user so that there is a defined volume between the earcups of the headphone or the headset and the head of the user. If however a user is wearing spectacles or sunglasses then on the one hand this can result in the volume between the head and the headphone/headset not being properly sealed off while on the other hand the wearer of spectacles with a circumaural headphone is often felt to be uncomfortable because the side arm of the spectacles is pressed against the head of the user by the ear cushion.

The German Patent and Trade Mark Office searched the following documents in the German patent application from which priority is claimed: U.S. Pat. No. 5,706,360 A; DE 10 2007 013 719 A1; US 2012/0278070 A1; U.S. Pat. No. 7,317,802 B2; US 2013/0129106 A1; US 2010/0119076 A1; JP 2012-244617 A and JP 2002-101483 A.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicidy recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112), such that applicant(s) reserve the right to disclaim, and hereby disclose a disclaimer of any previously described product, method of making the product, or process of using the product.

SUMMARY OF THE INVENTION

Thus an object of the present invention is to provide a headphone or a headset having active noise compensation, which can also be used comfortably by spectacles wearers.

Thus there is provided a headphone or headset comprising at least one housing, at least one microphone for detecting interference sound, at least one active noise compensation unit for implementing active noise compensation based on the interference sound detected by the at least one microphone and for the output of a compensation signal. The headphone or the headset has at least one electroacoustic reproduction transducer for output of the compensation signal from the noise compensation unit, and a circumaural ear cushion having a recess for receiving a spectacles side arm. The active noise compensation unit is adapted in noise compensation to take account of the effect of the recess in the ear cushion.

The invention concerns a notion of providing a headphone or a headset having a circumaural cushion, wherein the cushion has a recess adapted to accommodate a side arm of a pair of spectacles. In other words the position of the recess is so selected that it can extend around a spectacles side arm so that the pressure exerted on the spectacles side arm by the ear cushion is reduced or avoided.

In an aspect of the present invention the headphone or headset has an active noise compensation unit having a first microphone for the detection of interference sound outside the housing and optionally a second microphone for the detection of an interference sound or noise within the housing of the earcup or within the ear cushion.

According to an aspect of the present invention there can be provided an external microphone in the region of the spectacles side arm recess. An internal microphone can optionally be provided in front of an electroacoustic sound transducer, for example at a sound baffle.

According to a further aspect of the present invention an ear cushion of a headphone or headset is adapted to be interchangeable and the active noise compensation can switch over between a first operating mode for an ear cushion having a spectacles side arm recess and a second operating mode for the use of an ear cushion without a recess. Optionally switching over can be effected by a user or wearer of the headphone or headset.

According to a further aspect of the present invention there can be provided an identification in the ear cushion, which is detected by the headphone or the headset, so that it is possible to switch over between the first and second operating mode of active noise compensation in accordance with the identification in the ear cushion.

BRIEF DESCRIPTION OF THE DRAWINGS

FIG. 1 shows a diagrammatic sectional view of a headphone or a headset according to a first embodiment.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

FIG. 1 shows a diagrammatic sectional view of a headphone or a headset in accordance with a first embodiment. The headphone or headset has an active noise compensation unit 100 in a housing or earcup 150 of the headphone or headset and an electroacoustic sound transducer 140 within the housing 150. The headphone or headset has for example two housings/earcups 150 connected together by way of a hoop. One housing/earcup 150 is disposed on the left-hand ear and one is disposed on the right-hand ear. Provided in or at the housing 150 are at least one microphone, preferably at least two microphones (an internal microphone 130 and an external microphone 120). The external microphone 120 is provided at or in the housing 150 for detecting external sound and the internal microphone is provided within the housing 150 for detecting internal sound. Those microphones 120, 130 serve to detect interference sound or ambient noise and to pass that interference sound or ambient noise to the active noise compensation unit 100 which, based on those signals, implements active noise compensation and outputs a compensation signal to the electroacoustic reproduction transducer 140. Optionally there can be a control unit 170 for controlling the active noise compensation unit 100. In that respect the control unit 170 can optionally be switched over between a first and a second operating mode.

An ear cushion 160 can be fixed to the housing 150 of the headphone or headset. That ear cushion 160 is optionally a circumaural ear cushion so that the ear cushion 160 bears against a head 200 of a user.

In accordance with a first embodiment the ear cushion 160 has a recess 161 for a spectacles side arm 210. Optionally the recess 161 is so designed that it is not in contact with the spectacles side arm 210 or that it exerts only a low pressure on the spectacles side arm 210. The recess 161 can extend over the thickness of the ear cushion 160 so that a spectacles side arm can be received there.

In a first operating mode the active noise compensation unit 100 is adapted to implement active noise compensation based on the signals from the internal and external microphones 120, 130, wherein active noise compensation takes account of the recess 161 in the ear cushion 160.

In accordance with a second embodiment of the invention which can be based for example on the first embodiment, there is provided a headphone or headset which has at least one housing 150 with an active noise compensation unit 100, an electroacoustic reproduction transducer 140 and at least one microphone 120, 130. Different ear cushions 160 can be fixed to the housing 150. In other words the ear cushions 160 are designed to be interchangeable.

Thus an ear cushion with a spectacles side arm recess 161 or an ear cushion without such a spectacles side arm recess 161 can be fixed to the housing 150. If an ear cushion with a spectacles side arm recess 161 is fixed to the housing 150 then the active noise compensation unit 100 can be operated for example by means of the control unit 170 in the first operating mode, that is to say the active noise compensation function of the active noise compensation unit 100 takes account of the influence of the recess 161 in the ear cushion. The headphone or the headset is operated as described in the first embodiment.

In a second operating mode, that is to say if an ear cushion 160 without spectacles side arm recess is used, then the active noise compensation unit 100 can be operated in a second operating mode for example by means of the control unit 170, in which case the active noise compensation function of the active noise compensation unit 100 is optimized for the situation where there is no recess in the ear cushion and the ear cushion thus bears against a head of a user, along the entire periphery of the ear cushion.

The headphone or headset according to the invention is advantageous because it improves wearing comfort in particular for spectacles wearers of a headset or headphone according to the invention. A spectacles side arm is no longer pressed excessively firmly against a head of a user by the ear cushion. Rather, the recess 161 ensures that no or only a slight pressure is exerted on the spectacles side arm. In other words, there is provided a headphone or headset which makes it possible for no or only a slight pressure to be applied to the ear or to a spectacles side arm.

According to an aspect of the present invention the recess 161 is so designed that a spectacles side arm 110 is received in the recess 161 in contact-less or substantially contact-less relationship.

According to the invention there is provided a headphone or a headset having a pair of ear cushions and housings shown in FIG. 1.

According to the invention there is optionally provided an internal microphone 130 directly in front of the transducer 140, for example at a sound baffle, in order thereby to be used in a feedback control loop for active noise compensation. An external microphone 120 can optionally be provided in the region of or in the area around the spectacles side arm recess 161. Such a microphone can be used for a feedforward control loop for active noise compensation. Optionally there can be provided a further microphone which can be placed in an ear canal of a user or in the region of the ear canal. According to the invention it is provided that active noise compensation is ensured even at low frequencies although there is a spectacles side arm recess 161 in the circumaural cushion 160.

The provision of the spectacles side arm recess 161 in the ear cushion 160 can be advantageous in terms of wearing comfort because heat or moisture in the pinna is reduced thereby.

The headphone or the headset according to the invention can be used in particular in the aviation field or in the call center field as here there is often a noisy environment.

With the headphone or the headset according to the second embodiment it is possible to provide a headphone or a headset which can be adapted to the user, that is to say it is possible to adapt to whether the user is a spectacles wearer or not. That is effected by switching over active noise compensation in the first or second operating mode.

In the first operating mode the active noise compensation unit 100 operates with a first set of filter parameters and with a first dynamic characteristic. Those filter parameters and the dynamic characteristic are optimized for the situation where the ear cushion 160 has the spectacles side arm recess 161.

In the second operating mode the active noise compensation unit 100 operates with a second set of filter parameters and with a second dynamic characteristic. Those filter parameters and the dynamic characteristic are optimized for the situation where the ear cushion 160 does not have the spectacles side arm recess 161, that is to say the ear cushion is a completely encircling ear cushion 160.

According to an aspect of the present invention the headphone or the headset optionally has a sensor 180. The sensor 180 is adapted to detect whether placement of the earcup with the ear cushion 160 against the head of a user provides a closed volume or a volume which is open towards the exterior (that is to say having a spectacles side arm recess 161). Optionally the control unit 170 can switch over between the first and second operating modes in dependence on the output signals of the sensor 180. If therefore the sensor 180 detects that the volume is closed (that is to say there is no spectacles side arm recess 161) then the second operating mode is selected. If however the sensor 180 detects that the volume is not closed (that is to say the ear cushion 160 has the spectacles side arm recess 161) then the first operating mode is selected.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A headphone or headset comprising:

at least one housing;

at least one microphone configured to detect interference sound;

at least one active noise compensation unit configured to implement active noise compensation based on the interference sound detected by the at least one microphone, and to output a compensation signal;

at least one electroacoustic reproduction transducer configured to output the compensation signal from the noise compensation unit; and a circumaural ear cushion;

wherein, in a first operating mode:

the circumaural cushion comprises a recess configured to receive a spectacles side arm; and the active noise compensation unit is adapted to use a first set of filter parameters in the active noise compensation;

wherein, in a second operating mode:

the circumaural ear cushion is without a recess configured to receive a spectacles side arm; and the active noise compensation unit is adapted to utilize a second set of filter parameters in the active noise compensation; and wherein the first set of filter parameters is different from the second set of filter parameters.

2. The headphone or headset as set forth in claim 1, further comprising:

a sensor configured to detect whether the recess in the ear cushion is present;

wherein the active noise compensation unit is configured to operate in the first operating mode when it is detected by the sensor that the recess is present and wherein the active noise compensation unit is configured to operate in the second operating mode when it is detected by the sensor that the recess is not present.

3. The headphone or headset as set forth in claim 1:

wherein the at least one microphone is an internal microphone in the region of the electroacoustic reproduction transducer.

4. The headphone or headset as set forth in claim 1:

wherein the at least one microphone is an external microphone in the region of the recess in the ear cushion.

5. A headphone or headset comprising:

at least one electroacoustic reproduction transducer;

at least one microphone configured to detect interference sound;

at least one active noise compensation unit configured to implement active noise compensation based on the interference sound detected by the at least one microphone and to output a compensation signal to the electroacoustic reproduction transducer; and at least one housing which is adapted to receive an ear cushion that is configured to receive a spectacles side arm;

wherein, in a first operating mode:

the ear cushion receives the spectacles side arm such that a recess is created in the ear cushion; and the active noise compensation unit is adapted to utilize a first set of filter parameters to implement the active noise compensation; and wherein, in a second operating mode:

the ear cushion is without a recess created from the spectacles side arm;

the active noise compensation unit is adapted to utilize a second set of filter parameters to implement the active noise compensation; and wherein the first set of filter parameters is different from the second set of filter parameters.

6. The headphone or headset as set forth in claim 5, further comprising:

a sensor configured to detect whether the recess in the ear cushion is present;

wherein the active noise compensation unit is configured to operate in the first operating mode when it is detected by the sensor that the recess is present; and wherein the active noise compensation unit is configured to operate in the second operating mode when it is detected by the sensor that the recess is not present.

7. The headphone or headset as set forth in claim 5:

wherein the at least one microphone is an internal microphone in the region of the electroacoustic reproduction transducer.

8. The headphone or headset as set forth in claim 5:

wherein the at least one microphone is an external microphone in the region of the recess in the ear cushion.

9. A method of controlling an earphone or a headset which has at least one microphone for detecting interference sound and an ear cushion, comprising the steps:

detecting whether the ear cushion has a recess to receive a spectacles side arm;

detecting interference sound by the at least microphone;

implementing active noise compensation based on the interference sound detected by the at least one microphone in a first operating mode, when it is detected that the ear cushion has a recess, or in a second operating mode, when it is detected that the ear cushion does not have a recess, and outputting a corresponding compensation signal; and reproducing the compensation signal by the active noise compensation by at least one electroacoustic reproduction transducer;

wherein, in the first operating mode, a first set of filter parameters is utilized in the active noise compensation;

wherein, in the second operating mode, a second set of filter parameters is utilized in the active noise compensation; and wherein the first set of filter parameters is different from the second set of filter parameters.

* * * * *